| United States Patent [19] | [11] 3,960,940 |
| Elks et al. | [45] June 1, 1976 |

[54] PROCESS FOR THE PREPARATION OF D(−)-PENICILLAMINE AND SALTS THEREOF

[75] Inventors: Joseph Elks; Niall Galbraith Weir, both of London; Timothy Larry Gane, Harrow; Brian Burton, Ruislip, all of England

[73] Assignee: Glaxo Laboratories Limited, Greenford, England

[22] Filed: Aug. 14, 1974

[21] Appl. No.: 497,250

[30] Foreign Application Priority Data
Aug. 22, 1973 United Kingdom............... 39855/73

[52] U.S. Cl. .............................................. 260/534 S
[51] Int. Cl.² ..................................... C07C 149/243
[58] Field of Search................................. 260/534 S

[56] References Cited
UNITED STATES PATENTS
2,480,079   8/1949   Hunter et al. ............... 260/534 S X
3,666,770   5/1972   Bell et al. .................... 260/534 S X OTHER PUBLICATIONS
Asinger et al., Annual Report for 1967 of Landesant fur Forshung des Landes of Nordrhein–Westfalin, pp. 11–13.

Primary Examiner—Richard L. Raymond
Attorney, Agent, or Firm—Bacon & Thomas

[57] ABSTRACT

D(−)-Penicillamine and salts thereof may be prepared by reacting a 6-amino or blocked 6-amino penicillin e.g. penicillin G or penicillin V, or a salt thereof, with a hydrazine having two —NH-groups, or a salt or solvate thereof.

15 Claims, No Drawings

PROCESS FOR THE PREPARATION OF D(−)-PENICILLAMINE AND SALTS THEREOF

This invention relates to a novel process for the production of D-penicillamine and salts thereof.

Penicillamine, of formula

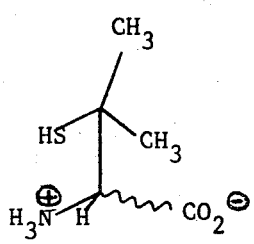   I is known to be useful in the treatment of cystinuria, Wilson's disease and rheumatoid diseases. It has, however, been observed that D(−)-penicillamine produces less serious side-effects than does L(+)-penicillamine and there is thus a demand for a commercially attractive process for preparing D-penicillamine.

Various methods for the production of D-penicillamine from penicillins have previously been proposed. Such processes generally proceed via penicilloic and/or penilloic acids as intermediates which may subsequently be converted into penicillamines. The penicillamine products may be precipitated from the reaction mixture by means of heavy metal cations such as mercury, and regenerated from the heavy metal complexes thus formed by treatment with another sulphur compound, such as hydrogen sulphide. However, the use of heavy metal compounds, which are potential poisonous contaminants, as well as the necessity for several stages in the reaction, render such processes commercially unattractive. Moreover, the heavy metal compounds may undergo undesirable reactions.

We have now found that D-penicillamine can be produced in good yield by reacting a penam-3-carboxylic acid or a salt or solvent thereof with a nucleophile capable of splitting the β-lactam ring to form a derivative of penicilloic acid in which the nucleophilic group is linked to the carbonyl group thereof and in that form is capable of reacting with an aldehyde. Since the penicilloic acid may be regarded as an aldehyde adduct of D-penicillamine, the effect of the nucleophile is to promote splitting of this adduct to yield D-penicillamine and a by-product formally produced by reaction of the nucleophilic group with the aldehyde group. This splitting process may be favoured by the presence of acid. We have found hydrazines especially useful nucleophiles; in these cases the by-products produced by reaction with the aldehyde group are pyrazolinones. Such hydrazines must possess two NH-groups, one to react initially to form a penicilloic acid hydrazide and a second to react with the above-mentioned aldehyde grouping.

We have thus found that it is possible to prepare D(−)-penicillamine of formula

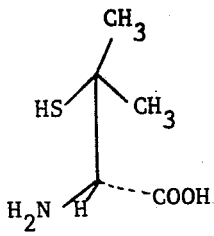   II and salts thereof by reaction of a penicillin of formula

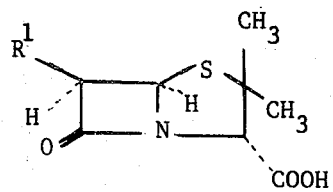   III or a salt or solvate thereof with a hydrazine having two NH-groups or a salt or solvate thereof, followed by isolation of the product of formula II.

In formula III, $R^1$ may be an amino group or, more preferably, a blocked amino group, for example one of the 6-acylamino groups which may be present in penicillins and which will normally contain 1–20 carbon atoms; it will advantageously be a phenylacetamido or phenoxyacetamido group.

The starting compound of formula III can be used in the form of an inorganic (e.g. sodium or potassium) or organic (eg. N-ethylpiperidine) salt thereof. Such salts are generally commercially available. Suitable solvates of compounds of formula III include, for example, the diisopropyl ether solvate of penicillin G.

In general, the penicillin compound of formula III is preferably fermentation derived and thus the most preferred compounds are penicillins G and V.

As stated above, the penicillin of formula III may be reacted with a hydrazine having two NH groups. Suitable substituted hydrazines include, for example, hydrazine itself; N-monoalkylhydrazines e.g. methylhydrazine; N,N'-dialkylhydrazines; and aryl hydrazines such as phenylhydrazine. Particularly high yields have been obtained using hydrazine and methylhydrazine. The hydrazine or substituted hydrazine may be used in the form of its hydrate or as a salt, e.g. a hydrochloride, hydrobromide, phosphate or sulphate. 0.5 to 10 equivalents, preferably 0.9 to 5 equivalents, of the hydrazine may be used, relative to the penicillin compound. The advantageous amount is 0.95 to 1.5 equivalents.

As indicated above, in general, the reaction takes place in two stages although it is preferably conducted in a single reaction vessel. Firstly, the hydrazine compound reacts with the penicillin compound to cleave the β-lactam ring and yield a penicilloic acid hydrazide. Subsequently the hydrazide undergoes cleavage to yield the desired D-penicillamine and a pyrazolinone by-product.

The first stage of the reaction is preferably effected at a temperature of from 0° to 100°C, advantageously 15° to 50°C, room temperature being particularly convenient although some initial heating may then be necessary in order to get the reactants into solution.

The second stage of the reaction is preferably effected at a temperature of from 20° to 120°C, advantageously 50° to 100°C.

As indicated above, the splitting process may be favoured by the presence of acid. About one equivalent of acid is preferred; in general mineral acids have given better results than organic acids and hydrochloric acid is especially suitable. Where relatively large equivalent amounts of mineral acid are used, however, neutralisation may be desirable to maximise precipitation of the desired penicillamine product. It will be appreciated that instead of adding acid with a hydrazine base, a corresponding salt may be used.

As a further precaution against the oxidation of the desired product, the reaction may be carried out in an oxygen-free or oxygen-reduced atmosphere, e.g. under nitrogen.

In order to obtain the maximum advantage from the simplicity of the present invention, ready isolation of the desired product is important. It is desirable that the solvent used be one in which the penicillamine is sparingly soluble. Suitable solvents of this type include nitriles such as acetonitrile and lower alkanols, e.g. alkanols containing from 1 to 6 carbon atoms, such as n-butanol and n-propanol. With such solvents, mineral acids such as hydrochloric acid are preferred where the first and/or second stage of the reaction is effected under acid conditions.

Where the initially precipitated product contains unwanted pyrazoline by-product, this may be removed by suspending the precipitate in a lower alcohol, for example ethanol or industrial methylated spirit, and introducing just sufficient strong acid, e.g. hydrochloric acid, to solubilise the D-penicillamine as an acid addition salt. Insoluble pyrazolinone can then be removed, e.g. by filtration, and the D-penicillamine can be reprecipitated by addition of a base such as triethylamine. The precise quantity of acid required can be determined by preliminary estimation of the quantity of D-penicillamine present, conveniently by measurement of optical rotation.

It is also possible to effect the reaction with hydrazine in the presence of solvents from which the pyrazolinone by-product is preferentially precipitated, e.g. water. Following removal of the pyrazolinone by-product, the desired product of formula II may be isolated from the reaction mixture using conventional techniques, such as evaporation to dryness followed by extraction of the residue with a non-solvent for the penicillamine compound whereby impurities are removed.

The process of the invention enables D-penicillamine and its salts to be prepared and readily isolated in a reaction which may be carried out in a single reaction vessel and essentially in a single stage, thus avoiding many of the disadvantages of prior art processes.

For a better understanding of the present invention, the following Examples are given by way of illustration only. In Examples 1 to 8, melting points were measured automatically in capillary tubes after insertion of the sample at 170°C with heating at 2° per minute. In Examples 9 to 12, melting points were measured using capillary tubes in an electrically heated melting point apparatus. Decomposition occurred at the melting points.

Unless otherwise stated, all $[\alpha]_D$ values pertain to solutions in $N$-NaOH, $c$ 0.9 to 1.1, at a temperature within the range 18° to 24°.

EXAMPLE 1

A suspension of (3R,5R,6R)-6-phenylacetamidopenicillanic acid (penicillin G), N-ethylpiperidine salt (6.7g, 15mmole) in water (30ml) was treated with hydrazine hydrate (0.73 ml, 15 mmole) and the resulting solution maintained at 22° for 1 hour. The solution was acidified to pH 3.2 with 0.5N-hydrochloric acid (ca 28ml) and precipitated material redissolved by warming. The mixture was refluxed in a nitrogen atmosphere for 45 minutes (material crystallising from solution after a few minutes reflux) and cooled. Precipitated material was removed by filtration and washed with water (10 ml) and dried in vacuo to give 4-phenylacetamido-$\delta^3$-pyrazolin-5-one as shiny plates, m.p. 218.6°. The filtrate (pH 7.1) was taken to pH 6 with 0.5 N-hydrochloric acid and freeze-dried. The resulting solid was stirred with methanol (20 ml) at 3° for 1 hour, and insoluble material collected by filtration and washed with cold methanol and dried in vacuo to give D(−)-penicillamine (1.1 g, 49%) as fine needles, m.p. 190.2°, $[\alpha]_D^{23}$ −66.7°. (Found: C,40.15; H,7.5; N,9.6; S,21.5. Calc. for $C_5H_{11}NO_2S$: C,40.2; H, 7.4; N.9.4; S,21.5%).

EXAMPLE 2

A suspension of penicillin G,N-ethylpiperidine salt (6.7g, 15mmole) in water (30 ml) was treated with hydrazine hydrate (0.73 ml, 15 mmole) and the resulting solution maintained at 22° for 1 hour. The solution was treated with acetic acid (3.5 ml, 60 mmole) (pH reached ca 4) and refluxed, in a nitrogen atmosphere, for 45 minutes. Precipitated 4-phenylacetamido-$\Delta^3$-pyrazolin-5-one was removed by filtration and the filtrate (pH ca 4) treated as in Example 1 to give D(−)-penicillamine (1g, 44.7%) as fine needles, m.p. 193.4° $[\alpha]_D^{22}$ −63.5°.

EXAMPLE 3

By the method described in Example 2 potassium (3R,5R,6R)-6-phenoxyacetamidopenicillanate(-peniciillin V, potassium salt) (5.08g, 13.1 mmole) gave 4-phenoxyacetamido-$\Delta^3$-pyrazolin-5-one as needles, m.p. 245° and D(−)- penicillamine (823 mg, 42.1%), m.p. 189.2°, $[\alpha]_D^{22}$ −62.6°.

EXAMPLE 4

A suspension of penicillin G, N-ethylpiperidine salt (13.4g, 30mmole) in acetonitrile (60 ml) was warmed to ca 45°. The mixture was stirred vigorously and treated slowly with hydrazine hydrate (1.45ml, ca 30mmole), then kept at 20° to 30° for 1½ hours. (a solution was obtained after 10 to 15 minutes). The solution was treated with acetic acid (3.5 ml, ca 60mmole) and refluxed, in a nitrogen atmosphere, for 4 hours. The mixture was cooled to ca 40° and the material which came out of solution during the reflux was collected and washed with cold acetonitrile, then dried in vacuo at 40° to give D(−)-penicillamine (2.2g, 49.2%) as colourless needles, m.p. 193.6°, $[\alpha]_D^{22}$ −62.9°.

EXAMPLE 5

By the method described in Example 4, penicillin G,N-ethylpiperidine salt (13.4 g) with n-butanol (60 ml), hydrazine hydrate (1.45 ml) and acetic acid (7ml, 120mmole) gave, after 45 minutes, at 98°, D(−)-penicillamine (1.45 g, 32.4%) as needles, m.p. 196.7°, $[\alpha]_D^{22}$ −63.2°.

EXAMPLE 6

With the method and quantities described in Example 5, penicillin G,N-ethylpiperidine salt (13.4 g) in n-propanol (60 ml) gave D(−)-penicillamine (700 mg, 15.6%) as needles, m.p. 196.2°, $[\alpha]_D^{22}$ −66°.

EXAMPLE 7

With the method and quantities described in Example 4, but with formic acid (2.26 ml, 60mmole) instead of acetic acid, penicillin G,N-ethylpiperidine salt (13.4 g), gave D(−)-penicillamine (1.17 g, 26%) as needles, m.p. 192°, $[\alpha]_D^{22}$ −62.5°.

EXAMPLE 8

With the method and quantities described in Example 4, but with no acetic acid, penicillin G,N-ethylpiperidine salt (13.4 g) gave D(−)-penicillamine (1.26g, 28.2%) as needles, m.p. 192.5°, $[\alpha]_D^{22}$ −61.9°.

EXAMPLE 9

A suspension of penicillin G, N-ethylpiperidine salt (13.4 g, 30 mmole) in acetonitrile (27 ml) was warmed to ca. 45°. Hydrazine hydrate (1.85 ml, ca 38 mmole) was added to the stirred mixture dropwise over 5 minutes to give a solution at the end of the addition, maintaining the mixture at 45° during the addition. The solution was stirred for 30 minutes without heat being applied, acetic acid (3.5 ml, ca. 60 mmole) was added, and the mixture refluxed in a nitrogen atmosphere for 4 hours. The mixture was cooled to 40° and the precipitated solid was filtered off, washed with acetonitrile (60 ml) and dried in vacuo to give D(−)-penicillamine (2.83 g, 63.2%) m.p. 204°–4.5°, $[\alpha]_D$ −62.6°.

EXAMPLE 10

By the method of Example 9, but using phenylhydrazine (3.24g, 30 mmole) and an increased amount of acetonitrile (60 ml), was obtained D(−)-penicillamine (1.9 g, 42.5%), m.p. 199.5°–200°, $[\alpha]_D$ −62.6°.

EXAMPLE 11

By the method of Example 10, but using methylhydrazine (1.41 g, ca 31 mmole), was obtained D(−)-penicillamine (3.4 g, 76.1%), m.p. 201°–201.5° $[\alpha]_D$ −62.6°.

EXAMPLE 12

Penicillin G, N-ethylpiperidine salt (268g, 0.60 mole) was suspended in acetonitrile (540 ml) and warmed to 45°C with stirring. Methylhydrazine (32.6 ml, ca. 0.62 mole) was added dropwise over 12 minutes and the temperature controlled at 45° by application of water cooling. After 15 minutes glacial acetic acid (70 ml, ca. 1.2 mole) was added. The system was flushed with nitrogen and stirred without heating under a nitrogen atmosphere for 30 minutes.

The solution was refluxed for 2 hours, cooled to 40° and filtered. The solid was washed with acetonitrile (500 ml) and dried in vacuo at 40° to constant weight to afford 153.3 g of white solid, $[\alpha]_D$ −29.9°.

The crude material (153.2 g) was suspended in IMS (600 ml) at 25°C with stirring and concentrated hydrochloric acid (41.2 ml) added dropwise. The mixture was stirred for 30 minutes and filtered. The solid was washed with IMS (50 ml) and dried in vacuo at 40° to constant weight to give 2-methyl-4-phenylacetamido-δ³-pyrazolin-5-one (56.3 g, 40.6% theory) m.p. 191°–193 °, $[\alpha]_D$ ±0°.

The combined mother liquors and washes were bulked and triethylamine (68.5 ml) added dropwise at room temperature. The mixture was stirred for 60 minutes with water cooling. The solid was removed by filtration, washed with IMS (50 ml) and dried in vacuo at 40°C to constant weight to afford D(−)- penicillamine (67.8 g, 75.8% theory) as a white solid, m.p. 197.5°–198°, $[\alpha]_D$ −62.6°.

EXAMPLE 13

Penicillin G, N-ethylpiperidine salt (134.0 g, 0.30 mole) was suspended in acetonitrile (600 ml) and warmed with stirring to 40°. Hydrazine hydrate (16.0 ml, 0.33 mole) was added dropwise over 5 minutes, followed by concentrated hydrochloric acid (27.5 ml, ca. 0.33 mole). The mixture was stirred under a blanket of nitrogen for 30 minutes and brought to reflux. After 4 hours at reflux the mixture was cooled to 40°, filtered and the solid washed with acetonitrile (600 ml) and dried at 40° in vacuo overnight to give 82.20 g of a white solid, $[\alpha]_D$ −30.1°.

The solid was suspended in stirred IMS (330 ml) and concentrated hydrochloric acid (22.2 ml) was added. The mixture was stirred for 15 minutes, filtered and the solid washed with IMS (50 ml) and dried at 40° in vacuo to give 34.96 g of 4-phenylacetamido-Δ³-pyrazolin-5-one.

The combined filtrate and wash was stirred at 10° under a blanket of nitrogen and triethylamine (37.0 ml) was added dropwise. The resultant suspension was stirred for 15 minutes at 10°, filtered and the solid washed with IMS (50 ml), ether (50 ml) and dried at 40° in vacuo overnight to give D(−)-penicillamine (37.37 g, 83.4% theory) m.p. 194°, $[\alpha]_D$ −62.2°.

EXAMPLE 14

Penicillin G, N-ethylpiperidine salt (40.2 g, 90 mmole) was suspended in acetonitrile (180 ml) and warmed to 40° with stirring. Hydrazine hydrate (4.35 ml, 90 mmole) was added dropwise over 5 minutes maintaining the temperature at 40°. Concentrated hydrochloric acid (7.5 ml, 90 mmole) was added causing immediate solution. The mixture was stirred without heating for 30 minutes under a blanket of nitrogen.

Glacial acetic acid (10.5 ml, 180 mmole) was added and the mixture was refluxed for 4 hours under nitrogen, cooled to 4° and filtered. The solid was washed with acetonitrile (180 ml) and dried in vacuo at 40° to constant weight to afford 20.56 g of white solid, $[\alpha]_D$ −31.9°.

The crude material (20.46 g) was suspended in IMS (80 ml) with stirring at 25°C and concentrated hydrochloric acid (5.87 ml) was added dropwise. The mixture was stirred for 30 minutes and filtered. The solid was washed with IMS (20 ml) and dried in vacuo at 40° to constant weight to give 4-phenylacetamido-Δ³-pyrazolin-5-one (8.14 g, 40.7% theory), m.p. 218°–219°, $[\alpha]_D = \pm 0°$.

The combined mother liquors and washes were bulked and triethylamine (9.80 ml) was added dropwise maintaining the temperature below 20° with water cooling. Stirring was continued for 15 minutes and D(−)-penicillamine was collected by filtration, washed with IMS (20 ml) and dried in vacuo at 40° to constant weight (9.58 g, 71.6% theory), m.p. 199°–200°, $[\alpha]_D$ −62.1°.

Tables 1 and 2 give results obtained in similar reactions in which the process conditions were varied.

TABLE 1

Variations on Example 10, using hydrazine bis (hydrochloride), or hydrazine hydrate in the presence of concentrated hydrochloric acid.

| Example No. | Hydrazine Reagent | Acid(s) added (equivalents with respect to penicillin) | Yield (%) | $[\alpha]_D$ (°) | Comments |
|---|---|---|---|---|---|
| 15 | Hydrazine Bis(hydrochloride) | Acetic (2) | 63.1 | −61.8 | N-Ethylpiperidine(NEP)(1 equivalent with respect to penicillin) added before hydrazine reagent. |
| 16 | Hydrazine Bis(hydrochloride) | Acetic (2) | 44.7 | −61.8 | NEP(2 equivalents) added before hydrazine reagent. |
| 17 | Hydrazine hydrate | Concentrated hydrochloric(1), Acetic (2) | 60.0 | A | Hydrochloric acid added just before hydrazine, acetic acid added just before reflux. |
| 18 | Hydrazine hydrate | Concentrated hydrochloric(1) Acetic (2) | 85.6 | A | Hydrochloric acid added after hydrazine, acetic acid added just before reflux. |
| 19 | Hydrazine hydrate | Concentrated hydrochloric(1) Acetic (2) | 76.2 | A | Both acids added just before reflux |
| 20 | Hydrazine hydrate | Concentrated hydrochloric(2) | 51.5 | −64.2 | Acid added after hydrazine. No D(−)penicillamine precipitated during reflux. NEP(1 equivalent) added at end of reflux to precipitate product. |

Note to Table A: D(−)Penicillamine was obtained mixed with 4-phenylacetamido-$\Delta^3$-pyrazolin-5-one. The yield was obtained by multiplying the theory yield by the purity of the product as determined from its specific rotation.

TABLE 2

Variations on Example 9 on 60 mmole scale, using methylhydrazine (ca 1 equivalent with respect to penicillin) in the presence of concentrated hydrochloric acid, and a shorter reaction time (2 hr).

| Example No. | Acid(s) added (equivalents with respect to penicillin) | Yield* (%) | Comments |
|---|---|---|---|
| 21 | Concentrated hydrochloric (½) | 75.0 | Acid added after hydrazine |
| 22 | Concentrated hydrochloric (1) | 82.1 | Acid added after hydrazine |
| 23 | Acetic (2) concentrated hydrochloric (½) | 85.0 | Acetic acid added after hydrazine to dissolve the penicillin then hydrochloric acid added. |

*Yield calculated as in Table 1.

TABLE 3

Variations on Example 13. Quantities of hydrazine hydrate and concentrated hydrochloric acid

| Example No. | Hydrazine Hydrate | Conc. hydrochloric acid | Yield* |
|---|---|---|---|
| | Equivalents with respect to penicillin | | |
| 13 (as standard) | 1.1 | 1.1 | 90.0 |
| 24 | 1.0 | 1.0 | 81.0 |
| 25 | 1.0 | 1.1 | 85.0 |
| 26 | 1.0 | 1.2 | 83.0 |
| 27 | 1.1 | 1.0 | 85.4 |
| 28 | 1.2 | 1.0 | 85.6 |
| 29 | 1.1 | 1.2 | 84.6 |

*yield calculated as in Table 1

We claim:

1. A process for the preparation of D(−)-penicillamine and salts thereof wherein a penicillin of formula

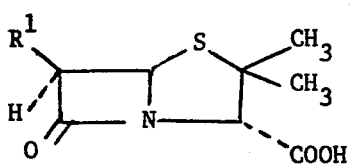

or a salt or solvate thereof, in which $R^1$ is selected from the group consisting of an amino group and a blocked amino group, is reacted with a hydrazine having two —NH-groups, or a salt or solvate thereof followed by isolation of the product.

2. The process according to claim 1 wherein the amino group is blocked with a phenylacetyl or phenoxyacetyl group.

3. The process according to claim 1 wherein the hydrazine is hydrazine or methylhydrazine.

4. The process according to claim 1 wherein 0.5 to 10 equivalents of the hydrazine relative to the penicillin are used.

5. The process according to claim 1 wherein reaction takes place in two stages, the first stage wherein a penicilloic acid hydrazide is formed being effected at from 15° to 50°C.

6. The process according to claim 5 wherein the second stage of the reaction in which penicillamine is formed is effected at a temperature of from 50° to 100°C.

7. The process according to claim 1 wherein mineral acid is present in the form of the free acid or in the form of a hydrazine salt.

8. The process according to claim 7 wherein one equivalent of acid relative to the penicillin compound is used.

9. The process according to claim 1 wherein reaction is carried out under an oxygen-free or oxygen-reduced atmosphere.

10. The process according to claim 1 wherein reaction is carried out in a solvent in which penicillamine is sparingly soluble.

11. The process according to claim 10 wherein the solvent is selected from the group consisting of acetonitrile, n-butanol and propanol.

12. The process according to claim 10 wherein the penicillamine is suspended in a lower alcohol in the presence of a strong acid to form an alcohol soluble salt thereof, insoluble by-products are removed and the D-penicillamine is precipitated by addition of base.

13. The process according to claim 1 wherein reaction is carried out in a solvent in which the reaction by-product is sparingly soluble.

14. The process according to claim 1 wherein the hydrazine is selected from the group consisting of hydrazine N-monalkyl-hydrazines, N,N'-dialkylhydrazines and aryl hydrazines.

15. The process according to claim 14 wherein the hydrazine is selected from the group consisting of hydrazine, methylhydrazine and phenylhydrazine.

* * * * *